(12) United States Patent
Kuipers

(10) Patent No.: US 11,580,871 B2
(45) Date of Patent: Feb. 14, 2023

(54) ASSESSMENT SYSTEM AND ASSESSMENT METHOD

(71) Applicant: Johan Ritser Kuipers, Wageningen (NL)

(72) Inventor: Johan Ritser Kuipers, Wageningen (NL)

( * ) Notice: Subject to any disclaimer, the term of this patent is extended or adjusted under 35 U.S.C. 154(b) by 192 days.

(21) Appl. No.: 16/503,082

(22) Filed: Jul. 3, 2019

(65) Prior Publication Data
US 2019/0325775 A1    Oct. 24, 2019

Related U.S. Application Data

(63) Continuation of application No. PCT/NL2018/050004, filed on Jan. 3, 2018.

(30) Foreign Application Priority Data

Jan. 4, 2017  (NL) ...................................... 2018125

(51) Int. Cl.
   *G09B 9/02*   (2006.01)
   *G09B 9/052*  (2006.01)
   (Continued)

(52) U.S. Cl.
   CPC .............. G09B 9/052 (2013.01); *A61B 5/18* (2013.01); *A61B 5/7264* (2013.01)

(58) Field of Classification Search
   CPC .......... A61B 5/18; A61B 5/7264; G09B 9/052
   (Continued)

(56) References Cited

U.S. PATENT DOCUMENTS

| 10,115,173 | B1* | 10/2018 | Manzella | ................ G06Q 50/26 |
| 2008/0254417 | A1* | 10/2008 | Mohamed | ................ G09B 9/04 |
| | | | | 434/69 |

(Continued)

FOREIGN PATENT DOCUMENTS

NL   1029007 C2   11/2006
NL   1032877 C2   11/2007

OTHER PUBLICATIONS

International Search Report dated Mar. 9, 2018 for International Patent Application No. PCT/NL2018/050004 filed Jan. 3, 2018. 4 pages.

*Primary Examiner* — Naomi J Small
(74) *Attorney, Agent, or Firm* — Kiri Lee Sharon; Foley & Lardner, LLP

(57) ABSTRACT

An assessment system is provided for assessing a performance of at least one autonomous actor in a dynamic environment. The system includes a computer program which, when operating on a data processing system, retrieves input selected from digital information, sensor data and a combination thereof, for detecting and classifying the at least one autonomous actor present in the dynamic environment; sets up a virtual reality simulation of the environment, and synchronizes the simulation with the environment. The program evaluates behavior of the actor in the environment, including measuring, analyzing and classifying actions and reactions of the actor in the simulation while the actor performs at least one predefined procedure in the environment; compares the behavior of the actor with a curriculum including at least one documented procedure and at least one documented performance value of the at least one predefined procedure; and outputs a qualification for the performance.

12 Claims, 1 Drawing Sheet

(51) Int. Cl.
*A61B 5/18* (2006.01)
*A61B 5/00* (2006.01)

(58) Field of Classification Search
USPC .............................................. 434/29
See application file for complete search history.

(56) References Cited

U.S. PATENT DOCUMENTS

| | | | |
|---|---|---|---|
| 2012/0021386 A1 | 1/2012 | Anderson et al. | |
| 2014/0272810 A1* | 9/2014 | Fields | G09B 5/125 |
| | | | 434/65 |
| 2015/0133820 A1* | 5/2015 | Zohar | G16H 20/30 |
| | | | 600/595 |

* cited by examiner

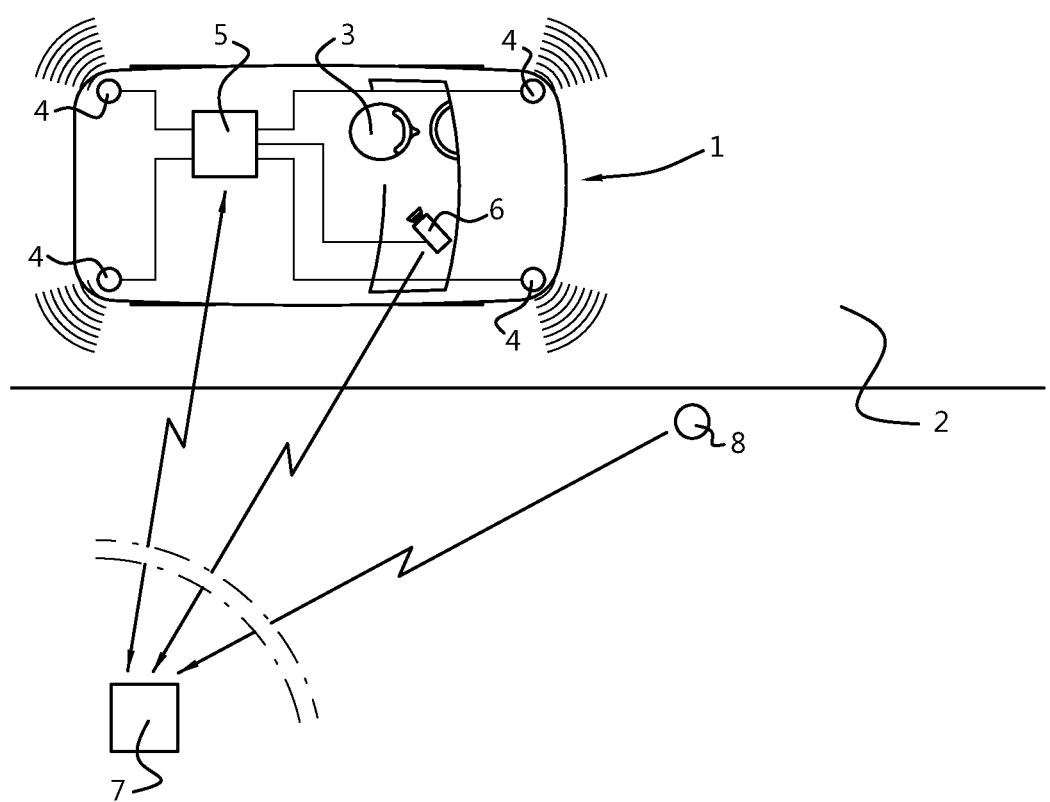

ASSESSMENT SYSTEM AND ASSESSMENT METHOD

CROSS-REFERENCE TO RELATED PATENT APPLICATIONS

This application is a continuation of International Patent Application No. PCT/NL2018/050004, filed Jan. 3, 2018, which claims the benefit of and priority to Netherlands Application No. 2018125, filed Jan. 4, 2017. The entire contents of each of these applications is incorporated by reference herein.

FIELD OF THE INVENTION

The invention relates to an assessment system, an assessment method, and a computer program product for an assessment method of system.

BACKGROUND OF THE INVENTION

Many processes and systems are becoming automated. As examples, autonomous vehicles driving on public roads are being introduced or robots assisting with the (health) care of elderly people. Evaluation of the performance of these systems related to the tasks they have to fulfill is complex.

And even the evaluation of the performance of human actors preforming tasks of procedures in a dynamic system or dynamic environment is complex. In the same sense as above, evaluating the performance of a human driver is complex. Usually, a beginning driver needs to pass a test in order to get a drivers license, an obligatory certificate. For this, the human driver has to perform a series of procedures in a dynamic environment in a test situation assessed by a human examiner. The value of these tests have proven to be limited. Scientific researches around the world reveals that novice drivers who pass the examination the first time are more involved in (deadly) accidents than the novice drivers who fail the first exam.

The examples above call for an improved assessment of actors performing procedures in a dynamic environment to support and improve certification The invention is related to inventions for the automated training of human operators. These inventions are described in the patents NL1029007 and NL1032877 from the inventor. A more detailed description of the inventions for automated training of human car drivers are found in the patents US 2012/0021386 and US 2014/0272810.

SUMMARY OF THE INVENTION

Hence, it is an aspect of the invention to provide an alternative assessment system, method and computer program product for this. In particular and/or furthermore, the invention provides a more independent assessment system and method with the purpose of certification of behavior. Without the certificate the assed entity cannot fulfill his/her/its tasks and/or goals.

The invention thus provides An assessment system for assessing a performance of at least one autonomous actor in a dynamic environment, said assessment system comprising a computer program which, when operating on a data processing system:
retrieves input selected from digital information, sensor data and a combination thereof, for detecting and classifying said at least one autonomous actor that is present in said dynamic environment;
set up a virtual reality simulation of said dynamic environment, and synchronizing said virtual reality simulation with said dynamic environment;
evaluate behavior of said at least one autonomous actor in said dynamic environment, said evaluating comprising measuring, analyzing and classifying actions and reactions of said at least one autonomous actor in said synchronized virtual reality simulation while said autonomous actor performs at least one predefined procedures in said dynamic environment;
compares said behavior of said at least one autonomous actor with a curriculum, said curriculum comprising at least one documented procedure and at least one documented performance value of said at least one predefined procedure;
output a qualification for said performance.

The invention furthermore provides an assessment method for assessment of a performance of at least one autonomous actor in a dynamic environment, said assessment method comprising:
retrieving input selected from digital information, sensor data and a combination thereof, for detecting and classifying said at least one autonomous actor that is present in said dynamic environment;
set up a virtual reality simulation of said dynamic environment, and synchronizing said virtual reality simulation with said dynamic environment;
evaluating behavior of said at least one autonomous actor in said dynamic environment, said evaluating comprising measuring, analyzing and classifying actions and reactions of said at least one autonomous actor in said synchronized virtual reality simulation while said autonomous actor performs at least one predefined procedures in said dynamic environment;
comparing said behavior of said at least one autonomous actor with a curriculum, said curriculum comprising at least one documented procedure and at least one documented performance value of said at least one predefined procedure;
outputting a qualification for said performance.

The invention further relates to a computer program product for assessment of a performance of at least one autonomous actor in a dynamic environment for the purpose of certification, said computer program, when operating on a data processing system:
retrieves input selected from digital information, sensor data and a combination thereof, for detecting and classifying said at least one autonomous actor that is present in said dynamic environment;
set up a virtual reality simulation of said dynamic environment, and synchronizing said virtual reality simulation with said dynamic environment;
evaluate behavior of said at least one autonomous actor in said dynamic environment, said evaluating comprising measuring, analyzing and classifying actions and reactions of said at least one autonomous actor in said synchronized virtual reality simulation while said autonomous actor performs at least one predefined procedures in said dynamic environment;
compares said behavior of said at least one autonomous actor with a curriculum, said curriculum comprising at least one documented procedure and at least one documented performance value of said at least one predefined procedure;
output a qualification for said performance.

In an embodiment, the said qualification is necessary for certification of the autonomous actor for performing predefined procedures.

The invention distinguishes from the state of the art inventions in headlines at least one of the following five manners. One; the invention is not limited for use related to human behavior. It also is applicable for animals, machines and software. Two; the purpose of the invention is not raising knowledge/training. The purpose in an embodiment is the certification of behavior. Three; the scope of the invention is not limited to operators of vehicles/driving. In an embodiment, the behavior cannot be executed without a certificate. Four: the invention is not limited by information collection from one point/place in the environment. Information collection can be done from arbitrary points/places. Five; The invention is not limited the real physical world as environment for assessment. The invention also uses 3D virtual environments/cyber worlds for assessment.

The invention in an embodiment is a critical part of a certification process related to behavior of actors A certificate is an official document of agreement giving rights to the holder, like a driving license or a vehicle type approval. A certificate can also comprise a digital certificate, enabling an actor to function or perform procedures, or for instance allow a computer program to run.

In an embodiment, the performance value is selected from an absolute performance value and a relative performance value and a combination thereof. In an embodiment, said absolute performance value being based on predefined parameters that are part of the curriculum, and said relative performance value being calculated based on at least one reference performance values of a peer group.

In an embodiment, the absolute performance value is mathematically calculated and said relative performance value is derived from a statistical evaluation. In an embodiment, the at least one performance value is applied to at least one selected from individual actions, reactions, on groups of actions, on groups of reactions and combinations thereof.

In an embodiment, the groups of actions and reactions are selected from one type of behavior, different kind of behaviors that are statistically correlated with each other, and combinations thereof.

In an embodiment, the assessment system uses performance data of a peer group related to said at least one predefined procedure to determine specific actions of the driver that correlates with faults related to accident involvement in said at least one predefined procedure.

In an embodiment, the dynamic environment is a traffic environment, said at least one autonomous actor is a driver, and said behavior comprises behavior of said driver while driving a vehicle, wherein said computer program furthermore retrieves data of said driver collected from previous attempts on said behavior. In an embodiment, the predefined procedure comprises a specific driving task, and said computer program furthermore retrieves data of said driver collected from previous attempts on said specific driving task.

In an embodiment, in case there is enough proof that the driver is capable and there is no indication for increased risk the autonomous assessment system will not change its status of observation and low resource consumption.

In an embodiment, the qualification enables issuing a certificate if said qualification results in a pass, which certificate enables said autonomous actor to continue operating in said dynamic environment.

A 3D environments as a reference for the assessment of behavior. The physical world is used and/or virtual (simulation) worlds can be used for the assessment. In an embodiment, a combination of the physical world and a representation/copy of the physical world in virtual reality is used for assessment of behavior. In such a embodiment, the static and dynamic components of the physical world and the virtual world are synchronized. The assessment itself is done in the virtual world. The assessment results produced in the virtual world can be used as input for certification and/or the results can be used to update the planning of the assessment process in the physical world.

The assessment system is for automated assessment of behavior of autonomous actors. These autonomous actors can be intelligent creatures like humans, or of animals. These autonomous actors can also comprise autonomous machines like robots, autonomous vehicles, and other autonomous control systems. In another embodiment, the autonomous actor can be a software agent. In this respect, autonomous relates to actors that can perform at least part of tasks themselves. An example is a software application driving a vehicle. The driver may receive instructions like "go left", or drive to a certain location from another actor. Such a driver is also called an autonomous actor.

The assessment system collects digital information and/or sensor data, referred to as the input. This input is used to classify the static environment that is hosting the automated assessment.

Information in the current context refers to ready to use, rich data. Sensor data means data that needs to be analyzed before it can be used for the automated assessment. Examples of sensor data are image data, sound data, radar data and liadar data.

The assessment system collects the information and/or sensor data to detect and classify autonomous actors and/or agents that are present in a dynamic environment. The assessment system measures, analyses and classifies actions and reactions of the autonomous actors in a role play. The assessment system observes the actions and the reactions of the one or more autonomous actors playing their role in a role play or a scenario. The assessment system compares the performance of the at least one autonomous actor with a documented procedure and documented performance values. The documented procedure together with the documented performance values are also referred to as curriculum.

The assessment system does these tasks of collecting, classifying, observing and comparing for individual autonomous actors and or groups of autonomous actors in relation to the environment and the curriculum.

The assessment system will also check the reliability of the information and the raw data and the curriculum. The assessment system uses intelligent 3D representations of the real world, also referred to as virtual reality, to perform analysis of actions and reactions of agents related to their environment. The assessment system examines the performance of the intelligent creature in relation to the performance of a peer group. The performance of the peer group on the curriculum is used as a reference for the performance of the intelligent creature. The advice or reported performance will be available as input for other intelligent systems or creatures that need this information as input for determining their actions and their behavior.

Assessment

In an embodiment the assessment system can make an assessment of the behavior of intelligent creatures without any interference of another human making the assessment. This assessment is necessary to determine if the intelligent creature, also referred to as the actor, is performing in a dynamic system or environment according to rules of such a dynamic environment. If this is not the case, the stability of the dynamic environment will decrease and the possibilities for errors in the dynamic environment will increase. Non-limiting examples for such dynamic environment or dynamic systems are the traffic system, the health care system, a factory and a power plant. In such systems, the assessment system can assess and even evaluate the behaviour or actors performing tasks in such systems. In particular, the assessment system can for instance assess tasks, in particular a combination of tasks that for behaviour, of the actor in the dynamic environment. For instance, the behaviour of a driver driving a car in a traffic environment like a highway, a city or the like can be assessed and the driver can be given a score or mark for his performance.

The assessment system is able to classify the actions and reactions of actors in good or false related to a curriculum. The assessment system is also capable to give a value to the good or false qualification. This value can be absolute or relative. In an embodiment, the absolute values or scores are based on predefined parameters that are part of the curriculum. In an embodiment, the relative values or scores are calculated based on reference values or scores of a peer group. In a particular embodiment, the absolute scores are mathematically calculated and the relative scores are statistically determined. Values or scores can be applied to individual actions or reactions but also on groups of actions and reactions. These groups of actions and reactions good can comprise one type of behavior but also relate to different kinds of behaviour that are statistically correlated with each other.

The assessment output related to the execution of procedures form the curriculum can be of different classifications like good or false or an absolute or relative score. The output is necessary as input for certification. The certificate will not be given in case the output of the assessment is not equal or below performance thresholds. These performance thresholds are described in the curriculum and/or certification requirements. The output of the assessment can also be used by the intelligent creatures in the environment to determine their reactions on the actions of the assessed actor. The output can also be used by the dynamic systems, containing the assessed actor, to react on the behavior of the intelligent actor. The actor can for example get permissions or restrictions based on the assessment.

Intelligent Creatures

The assessment system is designed for the assessment of intelligent creatures. Intelligent in the current context in particular relates to actions and reaction of creatures and which actions and reactions are the result of a decision process. The outcome of the decision process is not consistent. The results varies, and this can have positive or negative influences the desired stability of the dynamic system or dynamic environment in which the intelligent creatures are acting. The assessment is necessary to determine if the decision process of the intelligent creature, actor or agent, resulted in the desired actions.

Behavior

The proposed assessment system is able to assess behavior of actors and agents in a dynamic system. Behavior is the change of state of an intelligent creature. The change of state can be measured by comparing all kinds of parameters like position, speed, orientation, etc. over a period of time.

Environment

The assessment system uses a 3D environment as context for the assessment of behavior. The 3D environment represents or is the surrounding of the intelligent creature that directly or indirectly can have influence on the behavior. The 3D environment consists of components that separates spaces. The components can be static, meaning that their position don't varies and components of the 3D environment can be dynamic, meaning that their position can change. In case positions of the 3D environment components change, the spaces between components also will change.

The behavior of the intelligent creature or actors are related to the 3D environment. They have the intention to use the 3D environment and its components for orientation and navigation. For example they will seek for space before they change their position. Or they will use a component of the 3D environment to orientate and navigate.

The 3D environment can be made of physical elements and or virtual elements. The 3D environment may be completely real, or may be completely virtual, also referred to as virtual reality. Combinations of the real physical world and one or more virtual worlds are also possible, like augmented reality. The usage of a virtual representation of the physical world for assessment can have benefits like higher computational power, higher capacity, higher performance, higher intelligence. The virtual world has many benefits and less limitations compared to the physical world. In order to use a combination of the 3D physical and virtual world for assessment of behaviour synchronization of the static and dynamic components is necessary. For example in a virtual world it is relative easy to access information about the state of other static and dynamic components or their relations. Virtual sensors have less limitations than physical sensors. Therefor the combination of physical world and a virtual representation of this physical world can be beneficial for the assessment of behaviour. The physical world in such a case is used for observation of changes. The changes are uploaded to the virtual world. The changes are used to synchronize both worlds. After synchronization the assessment will be done in the virtual world. The assessment results can be used in the real world for adjustments, like instructions or other information that can influence the assessment of the behavior in the real world.

Observation

The proposed assessment system uses resources such as energy, like electricity, and processing units to perform, like CPU's and GPU's. Like most systems, here the assessment system is also restricted by its resources. Therefore, it uses strategies for efficient use of resources. These strategies can for instance comprise not performing all possible actions it knows at the same time. The assessment system for instance in an embodiment has the possibility to make selections of procedures it will assess based on real time observations and knowledge of earlier behavior of peers. This capability of observation and indirect reaction by comparing behavior with peer behavior is a fundamental principle for decrease of resource consumption and increase of performance. For example, in case a driver is driving towards a crossing and a navigation system indicates to turn right, the current assessment system will try to use performance data of a peer group related to this specific procedure to determine specific actions of the driver that correlates with faults related to accident involvement in this specific situation. The system will also try to use data of the driver collected from previous attempts on the specific driving task. In case there is enough proof the driver is capable and there is no indication for increased risk the autonomous assessment system will not change its status of observation and low resource consumption. In case the data reveal information about higher risks, the assessment system will change to a higher level of accuracy and monitor the driving task according to the curriculum. In case the drivers actions are not compliant then the system can interfere with an action like an advice for behavior change or it can take over the vehicle if necessary. This level of higher accuracy will take more resources. In case the resources are not sufficient, the assessment system may act according to its own procedures. It may then try to reduce the complexity that consumes the resources. For example, the assessment system can reduce speed of the vehicle indirectly by an advice for the driver or the assessment system can interfere directly by reducing speed of the vehicle. The same principle can be used in case of a higher risk than allowed by the curriculum or interpretation of the autonomous assessment system.

Sensors

The autonomous assessment system uses sensors to monitor and observe the intelligent creature and/or the actor or actors. Sensors can be mounted to static or moving components of the environment. The sensors can for instance be mounted in or on a wall or in or on a vehicle. Sensors collect raw data that can be transformed into information for the assessment system. The transformed sensor data, which then is information, is used by the system to determine the status of the environment components, the intelligent creature and the actors. The status means characteristics like position, orientation, shape, volume, color, brightness. The sensor could also reveal information that is more complex like identity, intention, desire. For the system, this information could help to decrease the use of resources and increase the performance. The sensors collect raw data with different techniques like voltage differences, radar, lidar, etc. The sensors comprise for instance a camera system, a motion sensor, absolute position sensor, acceleration sensor, direction sensor, speed sensor, air pressure sensor, humidity sensor, IT camera system, imaging system, gyroscopic sensor.

A major difference with other sensor based systems is that the rich sensor data, the information, not only is used for direct response but also is used for indirect response. The direct use of the sensor information leads to reactive behavior. Reactive behavior is in particular behavior that will always happen in case the information fits the formulated conditions of the behavior. The assessment system will not primarily react directly on the collected sensor information. It in particular uses the information to calibrate the 3D representation of the real world. The 3D representation is a simulation of the real world or a virtual world that enables the assessment system to use less resources and increase performance. For example in case an intelligent creature or actor is detected and the procedure it follows is clear, than it is not necessary to constantly determine the creature or actor and the procedure it follows. The assessment system can predict what is will happen based on the curriculum, environment and peer data. The accuracy of the prediction over time will decrease related to the situation. Therefore, after a certain period of time the assessment system should check if the conditions are in line with the predicted conditions. The actual sensor information is used for this measurement. This follows the procedure of observation. If there is a discrepancy between the sensor information and the predicted conditions the assessment system will update and increase the accuracy of the actual state of the environment, the intelligent creature and the actors. Doing so the use of resources will decrease and the performance of the assessment system will increase. The sensors information in this case is used to calibrate the 3D representation of the monitored or observed world and not to directly assess. The direct assessment is done in the 3D representation and leads to an indirect assessment of the environment where the sensors are collecting raw data.

Information

As explained above, raw data is not equal to information. The assessment system needs information to build a 3D representation of the environment, its components, the intelligent creature and the actors and calibrate all. Information means classified data, rich data. Classification is used to construct the 3D representation and calibrate it over time. The assessment system can classify raw data but this will take resources and decrease the performance of the assessment system. Therefore, the assessment system will first seek for information and if it is not available it will use raw data to classify and process raw data into information. For the classification of raw data it will use techniques that are common for data processing and 3D representation. For example the determination of dynamic actors. It can be calculate with bounding boxes, 3D volumes. The rhythm of parameter changes like size of the box will determine the object class. Image recognition can be used for determination of the state of indicators.

Communication between the assessment system and other information systems with or without sensors is also part of the information collection for the construction and calibration of the monitored and observed world and the 3D representation. For example multiple assessment systems can inform each other. In combination of alternatively, the intelligent creature and or actors can inform the assessment system and vice versa. Doing so the use of resources will decrease and the system performance will increase.

Environment components can also act as information suppliers and communicate with the assessment system and vice versa. For example, a traffic sign transmit information regarding for instance what it represents so the assessment system doesn't have to collect sensor data or sensor information. In an example, a road crossing can be provided with a current assessment system and inform the assessment system that assesses the intelligent creature what it status is. The assessment system that assesses the intelligent creature doesn't need to collect data about the status of the actors with help of sensors. Doing so the need for resources will decrease and the performance will increase.

In an embodiment, the invention further relates to an assessment system for assessing a performance of at least one autonomous actor in a dynamic environment, said assessment system comprising a computer program which, when operating on a data processing system:
  retrieves input selected from digital information, sensor data and a combination thereof, for detecting and classifying said at least one autonomous actor that is present in said dynamic environment;
  evaluate behavior of said at least one autonomous actor in said dynamic environment, said evaluating comprising measuring, analyzing and classifying actions and reactions of said at least one autonomous actor while said autonomous actor performs at least one predefined procedures in said dynamic environment;
  compares said behavior of said at least one autonomous actor with a curriculum, said curriculum comprising at least one documented procedure and at least one documented performance value of said at least one predefined procedure;
  output a qualification for said performance.

The terms "upstream" and "downstream" relate to an arrangement of items or features relative to the propagation of the light from a light generating means (here the especially the first light source), wherein relative to a first position within a beam of light from the light generating means, a second position in the beam of light closer to the light generating means is "upstream", and a third position within the beam of light further away from the light generating means is "downstream".

The term "substantially" when used herein, such as in "substantially all" or in "substantially consists", will be understood by the person skilled in the art. The term "substantially" may also include embodiments with "entirely", "completely", "all", etc. Hence, in embodiments the adjective substantially may also be removed. Where applicable, the term "substantially" may also relate to 90% or higher, such as 95% or higher, especially 99% or higher, even more especially 99.5% or higher, including 100%. The term "comprise" includes also embodiments wherein the term "comprises" means "consists of".

The term "functionally" will be understood by, and be clear to, a person skilled in the art. The term "substantially" as well as "functionally" may also include embodiments with "entirely", "completely", "all", etc. Hence, in embodiments the adjective functionally may also be removed. When used, for instance in "functionally parallel", a skilled person will understand that the adjective "functionally" includes the term substantially as explained above. Functionally in particular is to be understood to include a configuration of features that allows these features to function as if the adjective "functionally" was not present. The term "functionally" is intended to cover variations in the feature to which it refers, and which variations are such that in the functional use of the feature, possibly in combination with other features it relates to in the invention, that combination of features is able to operate or function. For instance, if an antenna is functionally coupled or functionally connected to a communication device, received electromagnetic signals that are receives by the antenna can be used by the communication device. The word "functionally" as for instance used in "functionally parallel" is used to cover exactly parallel, but also the embodiments that are covered by the word "substantially" explained above. For instance, "functionally parallel" relates to embodiments that in operation function as if the parts are for instance parallel. This covers embodiments for which it is clear to a skilled person that it operates within its intended field of use as if it were parallel.

Furthermore, the terms first, second, third and the like, when used in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The devices or apparatus herein are amongst others described during operation. As will be clear to the person skilled in the art, the invention is not limited to methods of operation or devices in operation.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "to comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device or apparatus claims enumerating several means, several of these means may be embodied by one and the same item of hardware. The mere fact that certain measures are recited in mutually different dependent claims does not indicate that a combination of these measures cannot be used to advantage.

The invention further applies to an apparatus or device comprising one or more of the characterizing features described in the description and/or shown in the attached drawings. The invention further pertains to a method or process comprising one or more of the characterizing features described in the description and/or shown in the attached drawings.

The various aspects discussed in this patent can be combined in order to provide additional advantages. Furthermore, some of the features can form the basis for one or more divisional applications.

BRIEF DESCRIPTION OF THE DRAWINGS

Embodiments of the invention will now be described, by way of example only, with reference to the accompanying schematic drawings in which corresponding reference symbols indicate corresponding parts, and in which:

The FIGURE schematically depicts an embodiment of the assessment system for assessing performance of an actor in a traffic environment.

The drawings are not necessarily on scale.

DESCRIPTION OF PREFERRED EMBODIMENTS

The FIGURE schematically depicts an embodiment of the assessment system, partly incorporated in a vehicle for assessing the performance of a (human) driver in a vehicle. Thus, in this example, the autonomous actor is a human driver, the dynamic environment is a car in everyday traffic, the procedure comprises several procedure that relate to driving a car, the performance can for instance relate to a driver license test, and the qualification can be a pass or fail of the driver license test.

In this example, the vehicle can be comprise one or more additional control systems that can assist the driver. The control system can vary from a simple warning system, like "lane assist", "collision warning", a more complex system like "cruise control" or "adaptive cruise control", or even an "automatic pilot" for some relative standardized procedures like parking or "driving on a highway" and that may only requires supervision and that allows manual override.

In the FIGURE, a vehicle 1 is on a road 2 and is driven by a driver 3 being said at least one autonomous actor. The dynamic environment thus is a vehicle being driven in traffic. The vehicle has various sensors 4. In general, the nature and specific sensors 4 are known to a skilled person. Usually, these sensors 4 transfer their data to a data processing system 5 inside the vehicle 1, and are thus functionally coupled to the data processing system 5. Such a data processing system 5 may provide support to the driver 3, or may take away tasks from the drives. In some cases, the data processing system may even comprise a complete auto-pilot system for driving the vehicle 1. The vehicle may further comprise one or more sensors, in particular assessment sensors 6, for measuring and/or recording actions and/or reactions from the driver. This assessment sensor may be functionally coupled to the data processing system 5.

In the FIGURE, an assessment system 7 is indicated outside and remove from the vehicle 1. The assessment system 7 may also be at least partly provided inside the vehicle. Thus, the assessment system 7 may be part of a distributed data processing system.

In the FIGURE, the assessment system 7 is functionally coupled to the data processing system in the vehicle. Here, the systems 5, 7 exchange data wirelessly. Furthermore, the at least one assessment sensor 6 is provided inside the vehicle 1 and is also functionally coupled to the assessment system 7.

In the FIGURE, additionally one or more assessment sensors 8 are indicated that are also functionally coupled to the assessment system 7.

In the example of the FIGURE, the assessment system 7 can assess the performance of the data system 5 for instance when it is capable of operating autonomously. The assessment system 7 can instead assess the performance of the driver 3. In another situation, the assessment system 7 may even assess the performance of the data processing system 5 and the driver3, and/or the interaction of the data processing system 5 and the driver 3.

It will also be clear that the above description and drawings are included to illustrate some embodiments of the invention, and not to limit the scope of protection. Starting from this disclosure, many more embodiments will be evident to a skilled person. These embodiments are within the scope of protection and the essence of this invention and are obvious combinations of prior art techniques and the disclosure of this patent.

The invention claimed is:

1. An assessment system for assessing a performance of at least one autonomous actor in a real-world dynamic environment, said assessment system comprising a non-transitory computer-readable medium configured to store instructions that are executable by a data processing system to cause operations to be carried out, the operations comprising:

retrieving input selected from digital information, sensor data and a combination thereof, for detecting and classifying said at least one autonomous actor that is present in said real-world dynamic environment;

setting up a virtual reality simulation of said real-world dynamic environment, and synchronizing said virtual reality simulation with said real-world dynamic environment using said retrieved input, and storing the virtual reality simulation in the data processing system;

evaluating behavior of said at least one autonomous actor in said real-world dynamic environment, said evaluating comprising retrieving said virtual simulation from the data processing system, and measuring, analyzing and classifying actions and reactions of said at least one autonomous actor in said synchronized virtual reality simulation while said at least one autonomous actor performs at least one predefined procedure in said real-world dynamic environment, wherein said evaluation comprises providing said measuring, analyzing and classifying actions and reactions in said retrieved virtual reality simulation after said actor has performed in said real-world dynamic environment so as to facilitate an independent assessment of the behavior, wherein the assessment is performed by the data processing system after the synchronization;

comparing said behavior of said at least one autonomous actor with a curriculum, said curriculum comprising at least one documented procedure and at least one documented performance value of said at least one predefined procedure; and outputting a qualification for said performance based on the assessment with respect to the at least one documented procedure, the qualification being associated with a certificate allowing the at least one autonomous actor to operate in said real-world dynamic environment.

2. The assessment system of claim 1, wherein said performance value is selected from an absolute performance value and a relative performance value and a combination thereof, in particular said absolute performance value being based on predefined parameters that are part of the curriculum, and said relative performance value being calculated based on at least one reference performance values of a peer group.

3. The assessment system of claim 2, wherein said absolute performance value is mathematically calculated and said relative performance value is derived from a statistical evaluation, wherein in particular said at least one performance value is applied to at least one selected from individual actions, reactions, on groups of actions, on groups of reactions and combinations thereof.

4. The assessment system of claim 1, wherein said groups of actions and reactions are selected from one type of behavior, different kind of behaviors that are statistically correlated with each other, and combinations thereof.

5. The assessment system of claim 1, wherein the operations further include determining a status of observation and a level of resource consumption, and said assessment system uses performance data of a peer group related to said at least one predefined procedure to determine specific actions of the at least one autonomous actor that correlates with faults related to accident involvement in said at least one predefined procedure.

6. The assessment system of claim 1, wherein said real-world dynamic environment is a traffic environment, said at least one autonomous actor is a driver, and said behaviour comprises behaviour of said driver while driving a vehicle, and wherein said operations further comprise retrieving data of said driver collected from previous attempts on said behaviour, wherein in particular said predefined procedure comprises a specific driving task, and retrieving data of said driver collected from previous attempts on said specific driving task.

7. The assessment system of claim 6, wherein upon determining that there is enough proof the driver is capable and there is no indication for increased risk, the autonomous assessment system does not change a status of observation and a level of resource consumption.

8. The assessment system of claim 1, wherein said qualification enables issuing the certificate responsive to said qualification resulting in a pass, which certificate enables said at least one autonomous actor to continue operating in said real-world dynamic environment.

9. An assessment method for assessment of a performance of at least one autonomous actor in a real-world dynamic environment, said assessment method being performable according to instructions stored in a non-transitory computer readable medium and executable by a data processing system, said assessment method comprising:

retrieving input selected from digital information, sensor data and a combination thereof, for detecting and classifying said at least one autonomous actor that is present in said real-world dynamic environment;

setting up a virtual reality simulation of said real-world dynamic environment, and synchronizing said virtual reality simulation with said real-world dynamic environment using said retrieved input, and storing the virtual reality simulation in the data processing system;

evaluating behavior of said at least one autonomous actor in said real-world dynamic environment, said evaluating comprising retrieving said virtual simulation from the data processing system, and measuring, analyzing and classifying actions and reactions of said at least one autonomous actor in said synchronized virtual reality simulation while said at least one autonomous actor performs at least one predefined procedure in said real world dynamic environment, wherein said evaluation comprises providing said measuring, analyzing and classifying actions and reactions in said retrieved virtual reality simulation after said actor has performed in said real-world dynamic environment so as to facilitate an independent assessment of the behavior, wherein the assessment is performed by the data processing system after the synchronization;

comparing said behaviour of said at least one autonomous actor with a curriculum, said curriculum comprising at least one documented procedure and at least one documented performance value of said at least one predefined procedure; and outputting a qualification for said performance based on the assessment with respect to the at least one documented procedure, the qualification being associated with a certificate allowing the at least one autonomous actor to operate in said real-world dynamic environment.

10. The assessment method of claim 9, wherein a certificate is issued in response to said qualification resulting in a pass, which certificate enables said at least one autonomous actor to continue operating in said real-world dynamic environment.

11. A non-transitory computer-readable medium configured to store instructions for assessment of a performance of at least one autonomous actor in a real-world dynamic environment for the purpose of certification, the instructions being executable by a data processing system to carry out operations comprising:

retrieving input selected from digital information, sensor data and a combination thereof, for detecting and classifying said at least one autonomous actor that is present in said real-world dynamic environment;

setting up a virtual reality simulation of said real-world dynamic environment, and synchronizing said virtual reality simulation with said real-world dynamic environment using said retrieved input, and storing the virtual reality simulation in the data processing system;

evaluating behavior of said at least one autonomous actor in said real-world dynamic environment, said evaluating comprising retrieving said virtual simulation from the data processing system, and measuring, analyzing and classifying actions and reactions of said at least one autonomous actor in said synchronized virtual reality simulation while said at least one autonomous actor performs at least one predefined procedure in said real world dynamic environment, wherein said evaluation comprises providing said measuring, analyzing and classifying actions and reactions in said retrieved virtual reality simulation after said actor has performed in said real-world dynamic environment so as to facilitate an independent assessment of the behavior, wherein the assessment is performed by the data processing system after the synchronization;

comparing said behaviour of said at least one autonomous actor with a curriculum, said curriculum comprising at least one documented procedure and at least one documented performance value of said at least one predefined procedure; and outputting a qualification for said performance based on the assessment with respect to the at least one documented procedure, the qualification being associated with a certificate allowing the at least one autonomous actor to operate in said real-world dynamic environment.

12. The non-transitory computer-readable medium of claim 11, wherein the operations further include issuing a digital certificate in response to said qualification resulting in a pass, which digital certificate enables said at least one autonomous actor to continue operating in said real-world dynamic environment.

\* \* \* \* \*